United States Patent
Görl et al.

(10) Patent No.: US 6,340,724 B1
(45) Date of Patent: Jan. 22, 2002

(54) POWDERED RUBBER CONTAINING MODIFIED FILLERS, PROCESS FOR THE PRODUCTION THEREOF AND USE THEREOF

(75) Inventors: Udo Görl, Bornheim-Roisdorf; Reinhard Stober, Hasselroth; Hartmut Lauer, Bad Soden-Salmünster; Uwe Ernst, Marl, all of (DE)

(73) Assignee: PKU Pulverkautschuk Union GmbH, Marl (GB)

( * ) Notice: Subject to any disclaimer, the term of this patent is extended or adjusted under 35 U.S.C. 154(b) by 0 days.

(21) Appl. No.: 09/293,935

(22) Filed: Apr. 19, 1999

(30) Foreign Application Priority Data

Apr. 17, 1998 (DE) .......................................... 198 16 972

(51) Int. Cl.$^7$ ............................. C08J 3/00; C08K 3/34; C08K 11/00; C08K 9/00; C08L 9/00
(52) U.S. Cl. ....................... 524/442; 523/200; 523/203; 523/204; 523/209; 523/212; 523/216; 524/492; 524/493; 524/494; 524/495; 524/496
(58) Field of Search .................................. 524/442, 492, 524/493, 494, 495, 496; 523/200, 203, 204, 209, 212, 216

(56) References Cited

U.S. PATENT DOCUMENTS

| | | | | |
|---|---|---|---|---|
| 3,842,111 A | * | 10/1974 | Meyer-Simon et al. | 260/448.2 E |
| 4,883,829 A | * | 11/1989 | Smigerski et al. | 523/334 |
| 5,116,886 A | * | 5/1992 | Wolff et al. | 523/209 |
| 5,159,009 A | * | 10/1992 | Wolff et al. | 524/495 |

* cited by examiner

*Primary Examiner*—Patrick D. Niland
(74) *Attorney, Agent, or Firm*—Pillsbury Winthrop LLP

(57) ABSTRACT

Finely divided powdered rubbers containing filler which remain free-flowing even after exposure to mechanical stresses and to a process for the production thereof, in which the rubber powder is obtained in two precipitation steps, and to the use of these powders for the production of vulcanizable rubber compounds. The fillers used, which are both precipitated silicas and carbon blacks known in the rubber art, are surface-modifed by organosilicon compounds.

7 Claims, No Drawings

POWDERED RUBBER CONTAINING MODIFIED FILLERS, PROCESS FOR THE PRODUCTION THEREOF AND USE THEREOF

CROSS REFERENCE TO RELATED APPLICATION

This application is based on German Patent Application DE 19816972.8 filed Apr. 17, 1998, the disclosure of which is incorporated herein by reference.

FIELD OF THE INVENTION

This invention relates to powdered rubbers containing fillers modified with organosilicon compounds, to a process for the production thereof and to the use thereof.

BACKGROUND OF THE INVENTION

Numerous publications have appeared relating to the aim and purpose of using powdered rubbers as well as to possible processes for the production thereof.

The explanation for the interest in powdered rubbers is readily evident from the processing techniques used in the rubber industry, where rubber compounds are produced in time-consuming processes with elevated inputs of energy and labour. The principal reason for this is that the rubber raw material is in bale form.

Comminuting the bale, intimate mixing with fillers, mineral oil plasticizers and vulcanization auxiliaries proceeds in roll mills or in internal mixers in two or more processing stages. The compound is generally stored between the stages. Downstream from the internal mixers or roll mills are extruder/pelletizers or extruder/roller dies. The only way out of this highly complex rubber processing method is to use an entirely novel processing technology. The use of free-flowing rubber powders has accordingly long been discussed as such powders would make it possible to process rubber compounds simply and rapidly in the same manner as powdered thermoplastics.

DE-PS 2822 148 discloses a process for the production of a powered rubber containing fillers.

According to this patent, an aqueous filler emulsion is added to a rubber latex, rubber solution or an aqueous emulsion of a rubber and the desired rubber powder is precipitated. Variants for preventing the resultant filler contents being determined by grain size, as occurs when this process is used, have been filed and, as DE-PS 3723 213 and DE-PS 3723 214, are part of the prior art. According to DE-PS 3723213, in a two-stage process, a quantity of ≧50% of the filler is initially incorporated into the rubber powder particles. In the second stage, the remainder of the filler is applied onto the so-called basic rubber grains. This may be considered a variant of dusting as no bond is created between the filler and rubber.

However, as E. T. Italiaander has pointed out (presentation 151, technical conference of the Rubber Division of the ACS, Anaheim, Calif., 6–9 May 1997 (GAK 6/1997 (50) 456–464)), despite the bright future predicted in the Delphi Report (Delphi Report, "Künftige Herstellverfahren in der Gummiindustrie", Rubber Journal, volume 154, no. 11, 20–34 (1972)) for powdered and pelletized rubbers and numerous attempts made by well-known polymer manufacturers from the mid 1970's until the early 1980's to produce powdered NBR, SBR/carbon black masterbatches and pelletized NR, the rubber bale remains the standard form in which rubber is supplied.

One disadvantage of known processes is firstly that a grinding operation is necessary in order to achieve a grain diameter of the filler particles of 10μm, which is considered essential to the quality of the final product.

However, this requires not only elevated energy input but also results in damage to the filler structure which, together with the active surface area, is a significant parameter for its effectiveness in rubber applications.

Secondly, the handling properties of prior art products suffer in that the particles stick together during storage.

The object of the invention is accordingly to provide a powdered rubber containing filler which is easily handled, together with a process for the production thereof.

SUMMARY OF THE INVENTION

The present invention provides a powdered rubber in which a filler, at least a proportion of which is modified by organosilicon compounds, is solidly bonded to the rubber matrix by a precipitation process. No confusion is thus possible with only superficially or adhesively coated rubber particles.

The powders according to the invention exhibit a narrow size distribution which is shifted towards smaller particle sizes as is known from the prior art (Kautschuk+Gummi+Kunststoffe 7, 28 (1975) 397–402). This fact facilitates processing of the powders. Moreover, due to the production process, the filler content of the individual particles is not determined by grain size.

The powdered rubbers contain from 20 to 250 phr, in particular from 50 to 100 phr, of filler (phr: parts per hundred parts of rubber), of which at least a proportion has been surfaced-modified using organosilicon compounds of the formula (I) known in the rubber art. The following, individually or as mixtures, have proved to be suitable types of rubber: natural rubber, emulsion SBR having a styrene fraction of 10 to 50%, butyl/acrylonitrile rubber, butyl rubbers, terpolymers prepared from ethylene, propylene (EPM) and unconjugated dienes (EPDM), butadiene rubbers, SBR, produced using a solution polymerization process, having styrene contents of 10 to 25%, as well as 1,2-vinyl constituent contents of 20 to 55% oand isoprene rubbers, in particular 3,4-polyisoprene.

In addition to these stated rubbers, the following elastomers may be considered, individually or as mixtures: carboxyl rubbers, epoxy rubbers, trans-polypentenamer, halogenated butyl rubbers, rubbers prepared from 2-chlorobutadiene, ethylene/vinyl acetate copolymers, epichlorohydrins, optionally also chemically modified natural rubber, such as for example epoxidized grades. Fillers which may be mentioned are the carbon blacks known from rubber processing and white fillers of a synthetic nature, such as, for example, precipitated silicas or natural fillers, such as, for example, siliceous chalk, clays etc.

Carbon blacks, as are generally used in rubber processing, are particularly suitable.

Such carbon blacks include furnace blacks, gas blacks and lamp backs having an iodine absorption value of 5 to 1000 $m^2/g$, a CTAB value of 15 to 600 $m^2/g$, a DBP absorption of 30 to 400 ml/100 g and a 24 M4 DBP value of 50 to 370 ml/100 g in a quantity of 5 to 250 parts, per 100 parts of rubber, preferably 20 to 150 parts, per 100 parts of rubber, more preferably 40 to 100 parts, per 100 parts of rubber.

Precipitated silicas known from the rubber art are also suitable.

These generally have an $N_2$ surface area, determined using the known BET method, of 35 to 700 $m^2/g$, a CTAB surface area of 30 to 500 m2/g, a DBP value of 150 to 400 ml/100 g. The product according to the invention contains these silicas in a quantity of 5 to 250 parts, preferably 20 to 100 parts, relative to 100 parts of rubber.

If white natural fillers are used, such as clays or siliceous chalks having an $N_2$ surface area of 2 to 35 $m^2/g$, they are used in a quantity of 5 to 350 parts, relative to 100 parts of rubber.

Filled rubber powders containing a mixture of silicas and carbon black are also suitable.

Unmodified fillers of the stated type are present in the rubber compounds claimed here only in addition to the fillers modified according to the invention. The proportion of the unmodified fillers depends upon the particular compound to be produced. In any event, the total filler content amounts to 20 to 250 phr. This quantity generally consists of 30 to 100%, preferably from 60 to 100%, of the modified fillers: silica and/or optionally carbon black. Surface-modification is generally performed using organosilicon compounds of the general formula

$$[R^1{}_{n-(RO)3-n}Si-(Alk)_m-(Ar)_p]q[B^1] \quad (I),$$

$$R^1{}_n(RO)_{3-n}Si-(Alk) \quad (II),$$

or $$R^1{}_n(RO)_{3-n}Si-(Alkenyl) \quad (III)$$

in which $B^1$: means —SCN, —SH, —Cl, —$NH_2$ (if q=1) or —SX— (if q=2)

R and $R^1$: mean an alkyl group having 1 to 4 carbon atoms, branched or unbranched, a phenyl residue, wherein all residues R and $R^1$ may each have the same or a different meaning, preferably an alkyl group, R: means $C_1$–$C_4$ alkyl, $C_1$–$C_4$ alkoxy group, branched or unbranched, n: means 0, 1 or 2, Alk: means a divalent linear or branched hydrocarbon residue having 1 to 6 carbon atoms, m: means 0 or 1

Ar: means an arylene residue having 6 to 12 C atoms p: means 0 or 1, providing that p, m and n do not simultaneously mean 0, x: means a number from 2 to 8, Alkyl: means a monovalent linear or branched saturated hydrocarbon residue having 1 to 20 carbon atoms, preferably 2 to 8 carbon atoms, Alkenyl: means a monovalent linear or branched unsaturated hydrocarbon residue having 2 to 20 carbon atoms, preferably 2 to 8 carbon atoms.

Examples of preferably used organosilanes are the bis(trialkoxysilyl-alkyl) oligosulfides which may be produced, for example, according to U.S. Pat. No. 3,842,111, such as bis-(trimethoxy-, triethoxy-, trimethoxyethoxy-, tripropoxy-, tributoxy-, tri-i-propoxy- and tri-i-butoxy-silyl-methyl) oligosulfides and specifically the di-, tri-, tetra-, penta-, hexasulfides etc., as well as bis-(2-trimethoxy-, triethoxy-, trimethoxyethoxy-, tripropoxy- and tri-n- and i-butoxy-ethyl) oligosulfides and in particular the di-, tri-, tetra-, penta-, hexasulfides etc., furthermore the bis-(3-trimethoxy-, triethoxy-, trimethoxyethoxy-, tripropoxy-, tri-n-butoxy- and tri-i-butoxysilyl-propyl) oligosulfides and again specifically the di-tri-, tetrasulfides etc. up to octasulfides, moreover the corresponding bis-(3-trialkoxy-silylisobutyl) oligosulfides, the corresponding bis-(4-trialkoxysilylbutyl) oligosulfides. Of these selected organosilanes of a relatively simple structure of the general formula I, those which are preferred are again the bis-(3-trimethoxy-, triethoxy- and tripropoxysilylpropyl) oligosulfides and specifically the di-, tri-, tetra- and pentasulfides, in particular the triethoxy compounds having 2, 3 or 4 sulfur atoms and mixtures thereof. In the general formula I, Alk means a divalent, linear or branched hydrocarbon residue, preferably a saturated alkylene residue having a linear carbon chain with 1 to 4 carbon atoms.

The silanes of the following structural formula are also particularly suitable

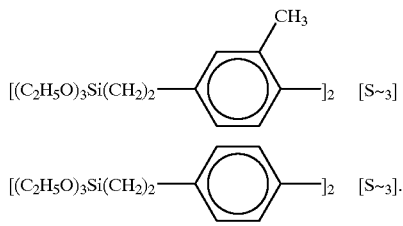

and the methoxy analogs thereof, which may be produced according to DE-AS 25 58191.

Nonionic, cationic and anionic surfactants are preferably used as surface-active substances. The concentration thereof in the suspension is 0.5 to 15 wt. %, preferably 0.5 to 5 wt. %, relative to the quantity of filler.

Examples of such surfactants are alkylphenol polyglycol ethers, alkyl polyglycol ethers, polyglycols, alkyltrimethylammonium salts, dialkyldimethylammonium salts, alkylbenzyltrimethylammomium salts, alkylbenzene sulfonates, alkyl hydrogen sulfates, alkyl sulfates.

In this manner, the entire quantity of organosilicon compounds necessary for the production of advantageous rubber compounds and vulcanizates may be incorporated by means of the modified filler. It is, however, possible to perform processes in which only a proportion of the organosilicon compounds are introduced in this manner and the remainder is added to the rubber compound in the conventional manner.

Such modified fillers are described, for example, in EP-B 0442 143, EP-B 0177 674 and in particular in pellet form in EP-A 0795 579 (white fillers) and in EP-B 0519 188 (carbon black).

Suitable bis(alkoxysilylalkyl)oligosulfanes have in particular proved to be those of the type of bis (trialkoxysilylalkyl)tetrasulfane and -disulfane.

The modified fillers known from the stated applications and patents and the organosilicon compounds mentioned therein are explicitly included in the present application as a constituent of the claimed compositions.

Apart from the above-stated fillers, the rubber powders according to the invention optionally contain known processing or vulcanization additives such as zinc oxide, zinc stearate, stearic acid, polyalcohols, polyamines, plasticizers, anti-aging agents to counter the action of heat, light or oxygen and ozone, reinforcing resins, flame retardants, such as for example $Al(OH)_3$ and $Mg(OH)_2$, pigments, various crosslinking chemicals and optionally sulfur in concentrations conventional in rubber processing.

The cross-section of the rubber powders according to the invention differs distinctly from that of products known from the prior art. The individual particles of the powdered rubber may consist of two zones which are intimately bonded together, concentrically enclose a center point and optionally have at least one of different filler content and different rubber content.

Depending upon the filler loading, filler particles are incorporated into the surface, such that the particles do not stick together, even under pressure, such as when several sacks are stacked.

This "inertization" of the surface should not be confused with the known technique of dusting tacky powders with fillers. These only superficially adhering fillers are rapidly detached when exposed to mechanical stress, for example in a conveying plant or on transfer into silos. The sticking and agglomeration of the finely divided powders, which it is the intention to avoid, then occurs despite the dusting. Unlike the tacky particles superficially coated with fillers as flow promoters as are known from the prior art, according to the invention, filler particles are incorporated into the surface during the precipitation process for the production of the rubber powder. Depending upon the filler loading with one or more of the above-stated fillers, the advisable distribution between the interior of the particles and an outer zone associated therewith is established.

In a product having an elevated filler loading ($\geq 80$ parts of filler per hundred parts of rubber), only 1 to 10 parts of this quantity of filler are incorporated in the outer grain zone. However, if the powdered rubber contains a total of <80 parts of filler per hundred parts of rubber, 10 to 20 parts thereof are incorporated in the outer grain zone (peripheral zone), i.e. do not merely adhere by less effective adhesive forces.

The distribution of the filler within the particles and in the so-called peripheral zone generally varies between these contents.

The greater the total filler content, the less is the need to suppress the tackiness of the powder by an increased concentration of filler in the peripheral zone.

The present invention also provides a process for the production of finely divided, rubber powders containing filler by precipitation from aqueous mixtures which contain filler in the form of suspensions, water-soluble salts of a metal of groups IIa, IIb, IIIa and VIII of the periodic system of elements and a rubber latex or aqueous emulsions of a rubber solution by addition of an acid, which process is characterized in that $\geq 50$ wt. % of the finely divided filler, at least a proportion of which has been surface-modified with an organosilicon compound according to the formulas (I), (II) or (III), are mixed with 0.1 to 6.5 parts by weight per 100 parts by weight of rubber of the stated water-soluble salts and a rubber latex or an aqueous emulsion of a rubber solution, the pH value of the mixture is reduced to a value in the range from 5.5 to 4.5 (first stage), the remainder of the finely divided filler in the form of a suspension is added and the pH value is reduced to approximately 3.2 (second stage), such that the rubber in the mixture is completely precipitated together with the filler.

The duration of the precipitation operation, which is determined by the pH value and the filler content, and the extent thereof may readily be determined by means of a series of measurements.

In the case of a rubber powder having an elevated filler loading ($\geq 80$ parts of filler phr), 1 to 10 parts of this quantity will generally be used as the remaining proportion in the second stage of precipitation of the rubber powder.

If the rubber powder contains less than 80 parts of filler phr, for example a total of only 50 parts phr, >10 to 20 parts of this quantity will be introduced into the mixture in the form of a suspension before conclusion of the precipitation operation.

In this manner, the fillers are incorporated into the outer grain zone (peripheral zone) of the rubber powder.

These proportions of the filler are thus not applied externally onto the individual rubber particles (cf. DE-PS 37 23213), but are integrated into the surface of the rubber.

This distribution of the filler and the manner in which the fillers are bonded to the rubber composition bring about the elevated flowability of the powders according to the invention and prevent sticking during storage of the powder, without these properties being lost on exposure to mechanical stresses during conveying, transfer into silos etc.

The above-stated carbon blacks are used as fillers in finely divided (fluffy) form. These carbon blacks generally have an average grain diameter of 1 to $9\mu m$, preferably of 1 to $8\mu m$, before they are suspended. This facilitates dispersion, such that aqueous suspensions containing filler particles of an average particle diameter of distinctly less than $10\mu m$ are obtained without elevated energy input. Precipitated silica may advantageously be used in the form of a filter cake which has been washed until salt-free.

Metal salts which may be used are those originating from elements of groups IIa, IIb, IIIa and VIII of the periodic system of elements. This division into groups corresponds to the former IUPAC recommendation (Periodisches System der Elemente, Verlag Chemie, Weinheim, 1985). Typical representatives are magnesium chloride, zinc sulfate, aluminum chloride, aluminum sulfate, iron chloride, iron sulfate, cobalt nitrate and nickel sulfate, wherein the salts of aluminum are preferred. Aluminum sulfate is particularly preferred.

The salts are used in a quantity of 0.1 to 6.5 parts by weight per 100 parts by weight of rubber. Acids suitable for establishing the defined pH values are primarily mineral acids, such as for example sulfuric acid, phosphoric acid and hydrochloric acid, wherein sulfuric acid is particularly preferred. However, carboxylic acids, such as for example formic and acetic acid, may also be used.

The quantity of acid is determined by the nature and quantity of the water-soluble metal salt, the filler, the rubber and the optionally present alkali metal silicate. This quantity may readily be determined by initial investigatory testing.

DETAILED DESCRIPTION OF THE PREFERRED EMBODIMENTS

According to a preferred embodiment of the process according to the invention, up to 5 parts by weight per 100 parts by weight of rubber of silica ($SiO_2$) are additionally used in the form of an alkali metal silicate solution, preferably as water glass having an $Na_2O:SiO_2$ molar ratio of 2:1 to 1:4. The alkali metal silicate solution may here be added both to the rubber component and to the filler suspension. It is preferably added to the rubber component, especially when the process is performed continuously.

The process according to the invention is generally performed as follows: first of all, a filler suspension is produced by dispersing a proportion, preferably $\geq 50\%$, of the filler present in the final product in water together with the metal salt and optionally the alkali metal silicate solution. The overall quantity of water is determined by the nature of the filler and the degree of digestion. In general, the water-insoluble constituents of the filler amount to approximately 6 wt. %. This value is not a binding restriction and both lower and higher quantities may be encountered. The maximum content is limited by the pumpability of the suspension.

The filler suspension produced in this manner is then intimately mixed, preferably in the presence of an emulsifier, with the rubber latex optionally containing alkali metal silicate solution or the aqueous emulsion of a rubber solution optionally containing alkali metal silicate solution. Known stirrers, such as for example propeller stirrers, are suitable for this purpose.

After mixing, a pH value in the range from 5.5 to 4.5 is first established while stirring is continued. This results in basic rubber grains having a constant filler content. The size of these basic grains is controlled by the selected quantity of metal salt in the range from 0.1 to 6.5 phr. Control is effected by the largest grain size being obtained with the lowest quantity of metal salt.

The remainder of the finely divided, optionally also modified white filler is added in the form of a suspension and the pH value is lowered to approximately 3.2.

The solids content of the latex used generally amounts to 20 to 25 wt. %. The solids content of the rubber solutions is generally 3 to 35 wt. %, that of the rubber emulsions generally from 5 to 30 wt. %.

These mixtures and the production thereof are known from the prior art.

When working up rubber powders having filler contents of ≧100 phr, it is advantageous to reduce the pH value down to 2.5 before phase separation. An acid from the above-stated group of acids is advantageously used for this purpose.

The process according to the invention may be performed both discontinuously and continuously.

The precipitated rubber powder is advantageously separated by means of a centrifuge and then dried to residual water content of generally ≦1%, in particular in a fluidized bed drier.

During the production process, further processing and/or vulcanization additives may be added to the rubber powder according to the invention in a quantity conventional for vulcanizable rubber compounds or also a smaller quantity.

The rubber powders according to the invention are used for the production of vulcanizable rubber compounds. The constituents necessary for producing the compound may all be present in the rubber powder. Preferably, however, the powders contain rubber of the above-stated types and fillers. They may, however, also be mixed in a conventional manner with other rubbers and fillers, if this is necessary for the desired rubber compound.

It is possible according to the invention to produce a finely divided rubber powder which is free-flowing and which also remains free-flowing after exposure to mechanical stresses (for example conveying, packaging). By virtue of the finely divided nature thereof, no grinding or other comminution measures are required to obtain finely divided dispersions.

These then give rise to the finely divided rubber powders, which may readily be processed, and to vulcanizates having improved properties.

EXAMPLES

A. The Examples describe the production and properties of vulcanizable rubber compounds which have been produced
1. using a rubber powder produced according to the invention (containing silica premodified with TESPT) and, in comparison thereto
2. using a rubber compound produced using silica premodified with TESPT.

B. Test standards used in the Examples:

|  | Unit | Standard |
|---|---|---|
| Tensile strength | Mpa | DIN 53504 |
| Elongation at break | % | DIN 53504 |
| Fracture energy | [J] |  |

C. Chemicals used in the Examples:

| | |
|---|---|
| TESPT | bis(triethoxysilylpropyl)tetrasulfane (Si69) (Degussa-Hüls AG) |
| Naftolen ZD | Plasticizer, aromatic hydrocarbons |
| 6PPD | N-1,3-dimethylbutyl-N'-phenylenediamine |
| CBS | N-cyclohexyl-2-benzothiazolesulfenamide |
| Coupsil 8113 | Precipitated silica surface-modified with 11.3 wt. % TESPT, relative to the silica |
| Vulkanox 4020 | Antioxidant based on phenylenediamine |
| Vulkacit CZ | Benzothiazyl-2-cyclohexylsulfenamide |
| Vulkacit D | Diphenylguanidine |
| Protektor G35P | ozone protection wax |

Example 1 comparison of a vulcanizate produced from powdered rubber according to the invention with a prior art vulcanizate

| Formulation (phr) | (E-SRB base stock, TESPT content, relative to silica: 11.3%) | |
|---|---|---|
|  | (1) | (2) |
| a) | | |
| Powdered rubber | 156 | |
| Coupsil 8113 |  | 56 |
| Buna SB 1500 |  | 100 |
| Naftolen ZD | 3 | 3 |
| ZnO | 2 | 2 |
| Stearic acid | 2 | 2 |
| Vulkanox 4020 | 1 | 1 |
| Protektor G35P | 1 | 1 |
| Sulfur | 1.5 | 1.5 |
| Vulkacit CZ | 1.7 | 1.7 |
| Vulkacit D | 2 | 2 |
| b) Scorching behavior (130° C.) | | |
| Scorch time (min) | 32.07 | 21.13 |
| Scorch time (min) | 41.57 | 26.3 |
| c) Tensile test on annular test piece (DIN 53504) | | |
| Tensile strength (MPa) | 21 | 19.1 |
| Elongation at break (%) | 590 | 530 |
| Fracture energy (I) | 161.7 | 135.6 |
| d) Dispersion test | | |
| Surface roughness | 1940 | 2750 | b) Scorching behavior (130° C.)

|  | (1) | (2) |
|---|---|---|
| Scorch time (min) | 32.07 | 21.13 |
| Scorch time (min) | 41.57 | 26.3 | c) Tensile test on annular test piece (DIN 53504)

|  | (1) | (2) |
|---|---|---|
| Tensile strength (MPa) | 21 | 19.1 |
| Elongation at break (%) | 590 | 530 |
| Fracture energy (I) | 161.7 | 135.6 | d) Dispersion test

|  | (1) | (2) |
|---|---|---|
| Surface roughness | 1940 | 2750 |

What is claimed is:

1. A finely divided rubber powder comprising:

a) a filler which is solidly bonded to the rubber matrix wherein said filler is modified with organosilicon compounds of the formulas (I), (II) or (III):

$$[R^1{}_{n-(RO)3-n}Si-(Alk)_m-(Ar)_p]q[B^1] \quad (I),$$

$$R^1{}_n(RO)_{3-n}Si-(Alk) \quad (II),$$

$$R^1{}_n(RO)_{3-n}Si-(Alkenyl) \quad (III); \text{ and}$$

b) a first zone and a second zone wherein said second zone surrounds and is intimately bonded with said first zone, and wherein said first zone and said second zone have a different filler versus rubber matrix content, in which q: means 1 or 2

$B^1$: means —SCN, —SH, —Cl, —NH2 (if q=1) or —Sx— (if q=2)

R and $R^1$: mean an alkyl group having 1 to 4 carbon atoms branched or unbranched, or a phenyl residue, wherein all residues R and $R^1$ may each have the same or a different meaning, n: means 0, 1 or 2, Alk: means a divalent linear or branched hydrocarbon residue having 1 to 6 carbon atoms, m: means 0 or 1

Ar: means an arylene residue having 6 to 12 C atoms p: means 0 or 1, provided that p and n do not simultaneously mean 0, x: means a number from 2 to 8, Alkyl: means a monovalent linear or branched saturated hydrocarbon residue having 1 to 20 carbon atoms, Alkenyl: means a monovalent linear or branched unsaturated hydrocarbon residue having 1 to 20 carbon atoms.

2. Finely divided rubber powder according to claim 1, comprising said modified fillers and unmodified fillers in a total amount of 20 to 250 phr.

3. Finely divided rubber powder according to claim 1, comprising 5 to 200 phr of a precipitated silica modified with an organosilicon compound as said modified filler.

4. Finely divided rubber powder according to claim 1, comprising 20 to 250 phr of a carbon black modified with an organosilicon compound and optionally unmodified carbon black as filler.

5. Finely divided rubber powder according to claim 1, comprising modified silica, carbon black and optionally unmodified silica in a total quantity of 5 to 250 phr as fillers.

6. Finely divided rubber powder according to claim 1, further comprising conventional processing additives and vulcanization additives.

7. The finely divided rubber powder according to claim 1, wherein the first zone and the second zone are spherical in shape.

* * * * *